United States Patent
Trabold et al.

(10) Patent No.: US 7,181,781 B1
(45) Date of Patent: Feb. 27, 2007

(54) FEMALE URINAL FUNNEL

(76) Inventors: Eric W. Trabold, 6406 Deer Ridge La., Columbus, OH (US) 43229; Joanne A. Trabold, 6406 Deer Ridge La., Columbus, OH (US) 43229; Joseph J. Leuser, 9015 N. 86th Pl., Scottsdale, AZ (US) 85258

( * ) Notice: Subject to any disclaimer, the term of this patent is extended or adjusted under 35 U.S.C. 154(b) by 0 days.

(21) Appl. No.: 11/418,567

(22) Filed: May 6, 2006

(51) Int. Cl.
*A47K 11/00* (2006.01)

(52) U.S. Cl. .................. 4/144.4; 4/144.3; 4/144.1; 604/317; 604/329

(58) Field of Classification Search ...... 4/144.1–144.4; 604/327, 317, 329, 331, 330
See application file for complete search history.

(56) References Cited

U.S. PATENT DOCUMENTS

| | | | | |
|---|---|---|---|---|
| 4,568,339 A * | 2/1986 | Steer | .......................... | 604/329 |
| 4,610,675 A * | 9/1986 | Triunfol | ..................... | 604/329 |
| 4,771,484 A * | 9/1988 | Mozell | ........................ | 4/144.4 |
| 4,911,698 A * | 3/1990 | Wapner | ....................... | 604/329 |
| 4,936,838 A * | 6/1990 | Cross et al. | ................. | 604/329 |
| 5,295,983 A * | 3/1994 | Kubo | .......................... | 604/329 |
| 5,848,993 A * | 12/1998 | Tanhehco et al. | ........... | 604/227 |
| 5,893,176 A * | 4/1999 | Magiera et al. | .............. | 4/144.4 |
| 6,922,852 B1 * | 8/2005 | Blum | ......................... | 4/144.4 |
| 2006/0149195 A1 * | 7/2006 | Oprandi | ...................... | 604/329 |
| 2006/0155214 A1 * | 7/2006 | Wightman | .................. | 600/574 |

FOREIGN PATENT DOCUMENTS

GB  2232597 A  * 12/1990

* cited by examiner

Primary Examiner—Khoa D. Huynh (57) ABSTRACT

Female urinal funnel with a rigid, essentially ovoid funnel shape. The funnel shape has side walls that extend vertically down from the entrance lip and then curve inwardly at approximately a ninety degree angle forming a flange that terminates at a centrally located exit orifice. The flange includes a pair of concave finger retaining channels located horizontally at the flanges upper and lower portions and a pair of concave finger retaining channels located vertically at the flanges left and right portions. A resilient water resistant panel shaped to fit snuggly over the labia majora of a female person conforms to the plane of the inside perimeter of the inlet edge of the funnel and extends outward approximately half an inch and having a centrally located ovoid aperture at the center of the panel to allow for urine to exit from the female and into the funnel.

2 Claims, 8 Drawing Sheets

FEMALE URINAL FUNNEL

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of urinal devices and more specifically to female urinal funnel.

There are circumstances where a woman must urinate when not having access to a standard toilet. One such circumstance is when a woman is confined to a bed such as in a hospital environment.

Currently, most female hospital patients who can not make their way to a standard toilet, are fitted with a catheter that is inserted into the vagina and is then attached by a hose to a urine collection bag. There have also been external catheters designed that make use of a funnel type device to be held in place around the labia majora to direct urine to an outlet hose and collection bag.

Patents granted within this category include D418918 by Cunningham, 5893176 by Magiera et al, 4771484 by Mozell, 4270539 by Michaud, 4846819 by Welch and D0466210 by Levinson. However there is a deficiency in the prior technology in that the effective means of physically holding the funnel shape firmly around the labia majora during use is compromised by the fact that the design of the funnel does not automatically guide the user to the most effective finger placement locations on the flange of the funnel and hence, increases the risk of urine leaking out of the inlet edge of the funnel thereby creating discomfort for the user and extra work for the nurse or care giver.

BRIEF SUMMARY OF THE INVENTION

The primary object of the invention is to provide a female urinal funnel that allows for ease of leak free retention by the user's fingers.

Another object of the invention is to provide a female urinal funnel that allows the user to employ either a horizontal holding technique or a vertical holding technique.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed female urinal funnel comprising: a rigid, essentially ovoid funnel shape whose perimeter entrance lip has a narrower diameter at its lower portion and a wider diameter at its upper portion, said funnel shape having side walls that extend vertically down from said entrance lip and then curve inwardly at approximately a ninety degree angle forming a flange that terminates at a centrally located exit orifice, said flange including a pair of concave finger retaining channels located horizontally at the flanges upper and lower portions and said flange including a pair of concave finger retaining channels located vertically at the flanges left and right portions.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
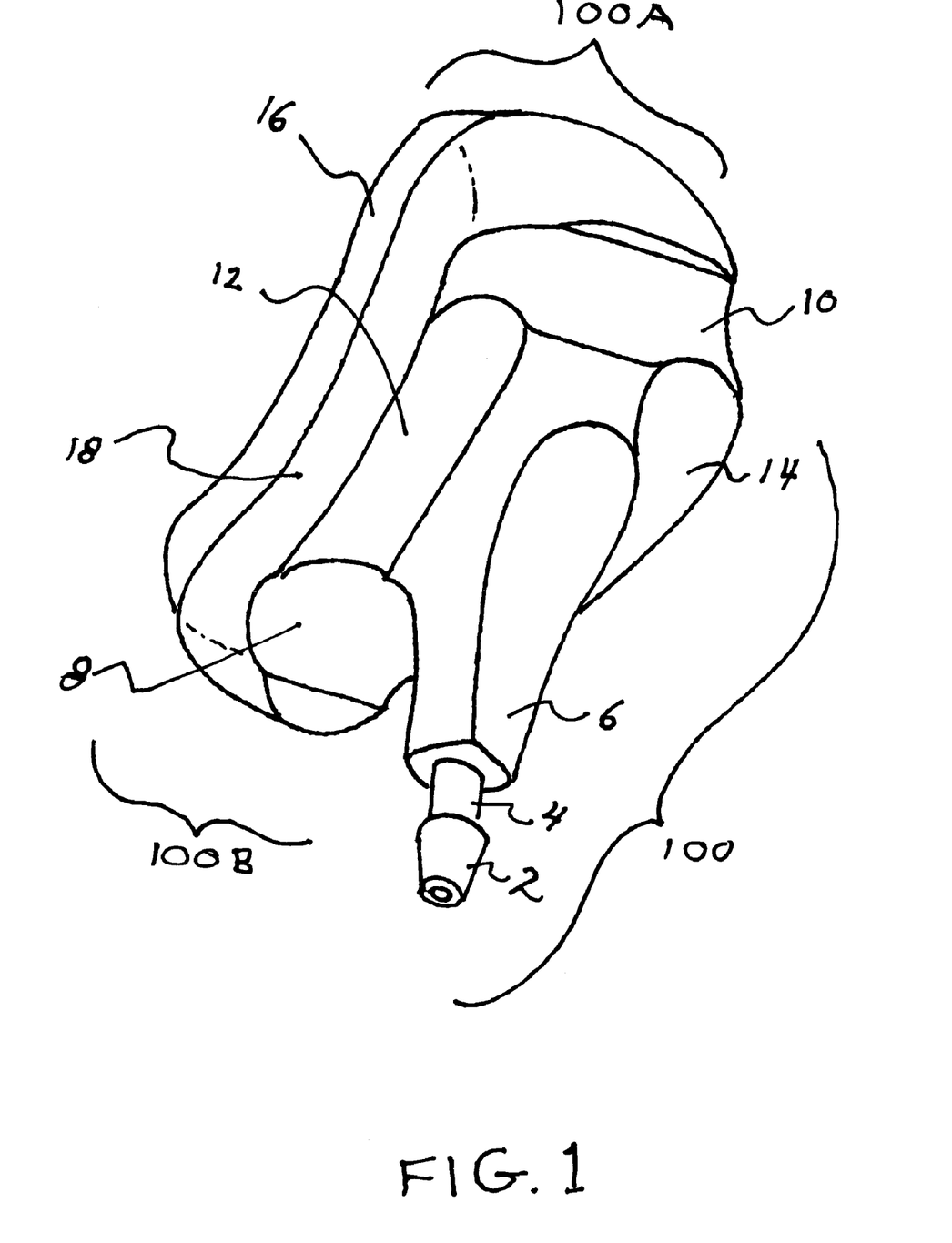
FIG. 1 is a top perspective view of the invention.

Referring now to FIG. 1 we see a top perspective view of the invention 100. The primary portion of the invention is the ovoid funnel shape comprised of an upper wide diameter portion 100A, and a lower narrower diameter portion 100B. A resilient panel 16 protrudes approximately one half of one inch beyond the inlet edge of the funnel 100, B. The funnel includes sidewalls 18 that extend vertically down from the inlet edge or perimeter entrance lip and then curve inwardly at approximately a ninety degree angle forming the bottom of the funnel. The bottom is sculpted into horizontal and vertical concave finger retaining channels 8, 10, 12, 14. A central funnel exit portion is comprised of hollow tapering portion 6 which terminates in barbed hose retaining tube 4, 2. A standard half inch diameter flexible hose can be attached to the retaining tube 2,4 and terminate into a standard urine collection bag not shown.

Figure 2:
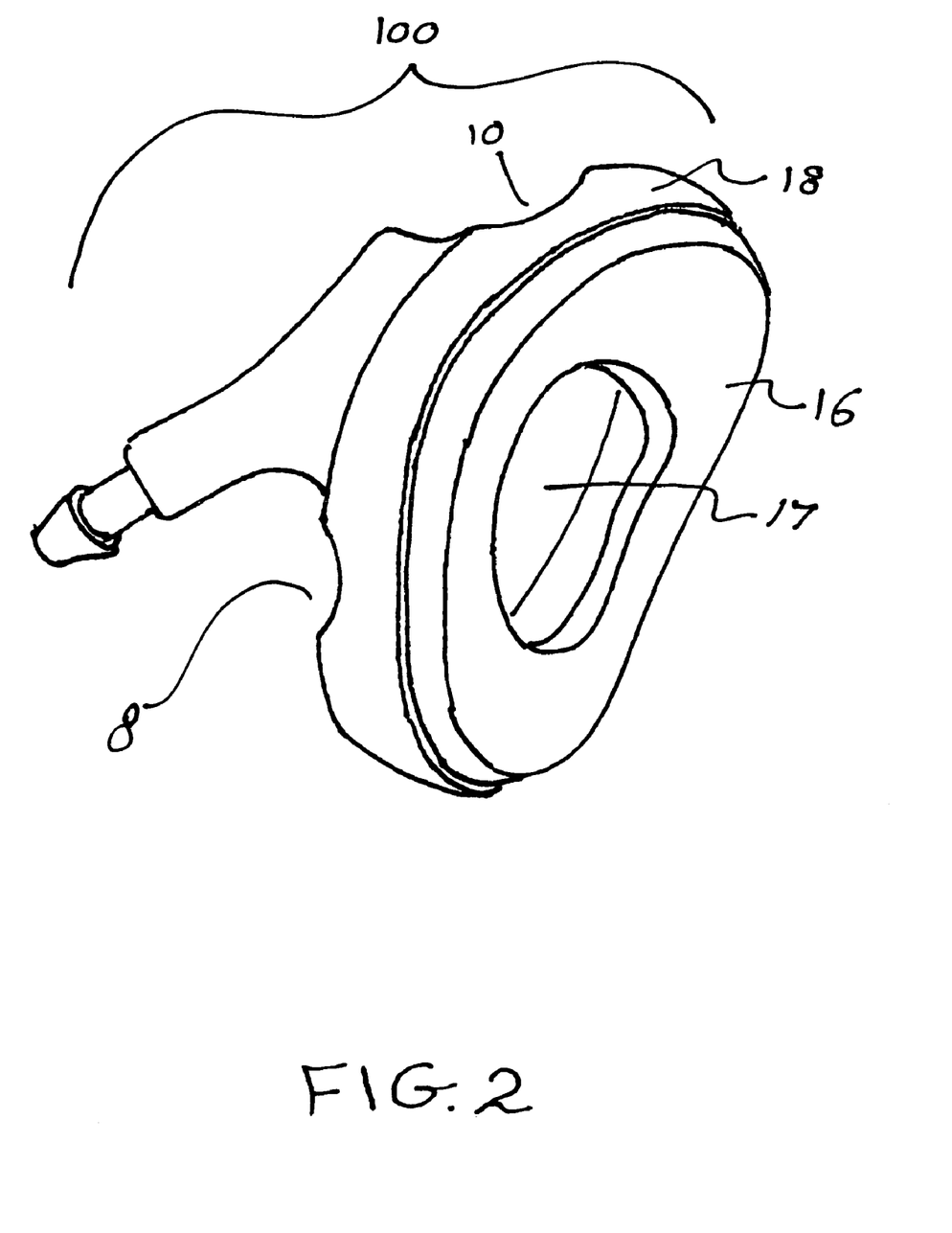
FIG. 2 is a bottom perspective view of the invention.

FIG. 2 shows a bottom perspective view of the invention 100. Resilient panel 16 is clearly seen and includes an ovoid aperture 17 which acts as an inlet port for female urine.

Figure 3:
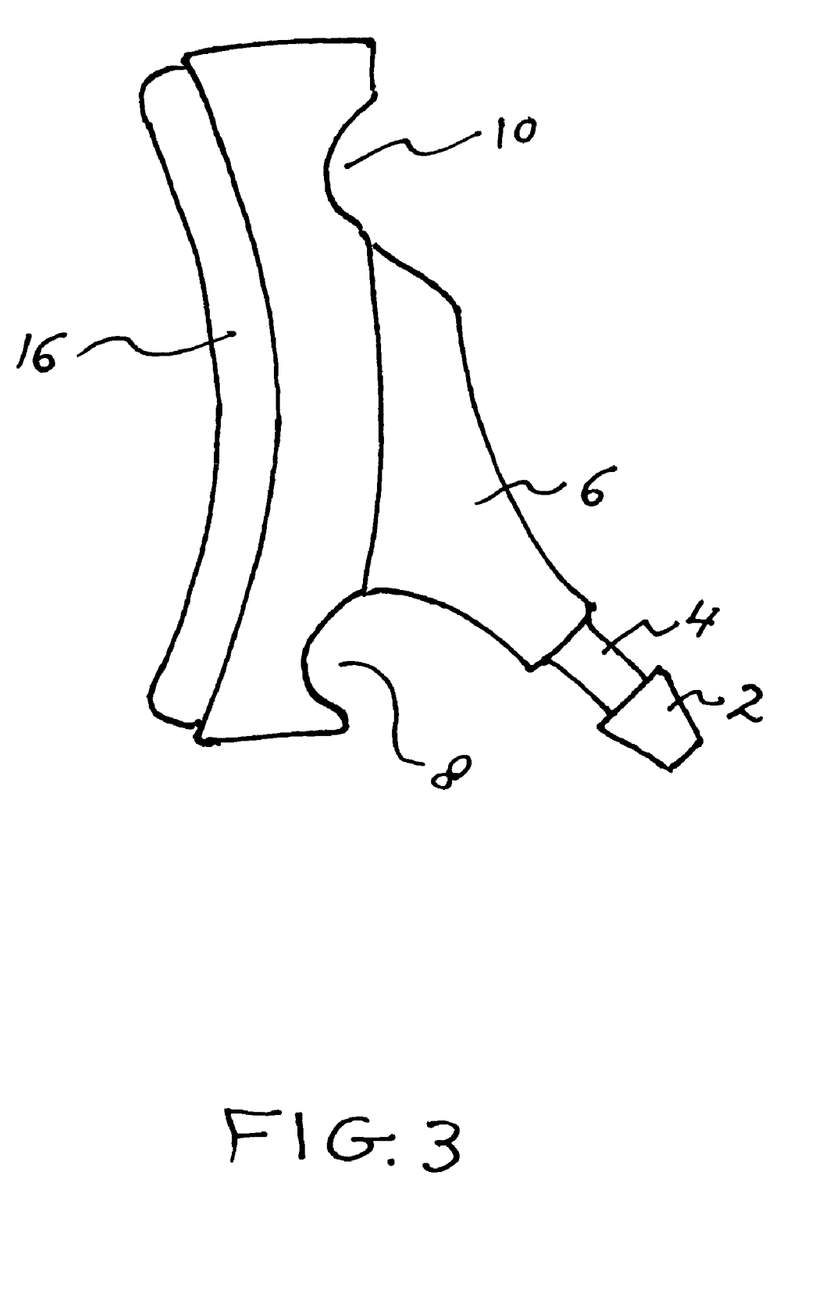
FIG. 3 is a side view of the invention.

FIG. 3 shows a side view of the invention 100 which clearly shows the finger retaining channels 8, 10. Additionally, this view shows that funnel exit portion 6 is angled downward with respect to the entrance panel 16 and approximately sixty degrees. This angle helps the exiting urine flow freely to a urine collection bag. The curve of panel 16 is designed to fit snuggly onto the vaginal area of a woman.

Figure 4:
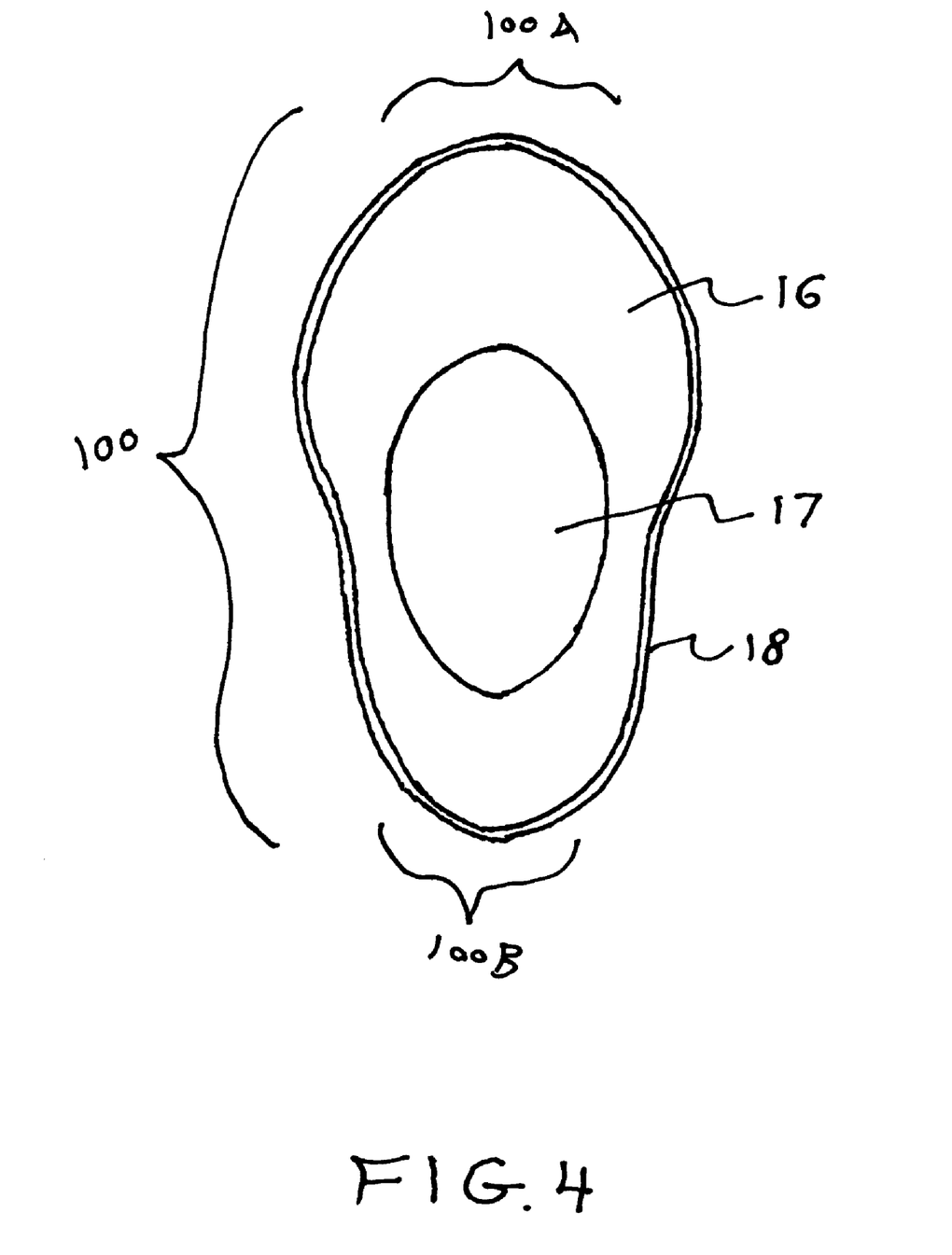
FIG. 4 is a bottom view of the invention.

FIG. 4 is a bottom view of the invention 100 showing the edge perimeter of funnel portion. The shape is designed to fit comfortably on a woman's vaginal area without cutting into the user's legs.

Figure 5:
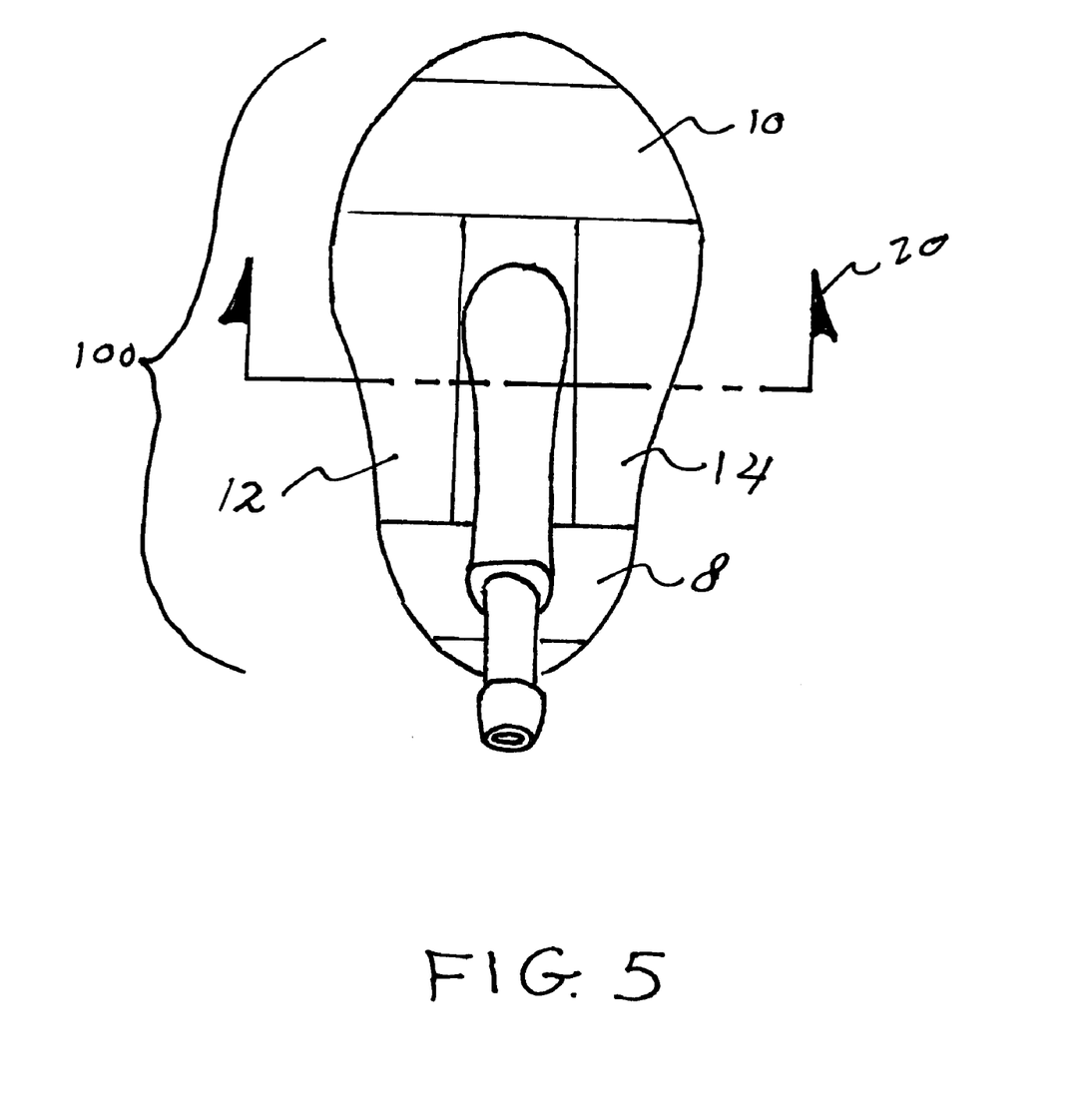
FIG. 5 is a top view of the invention.
Figure 6:
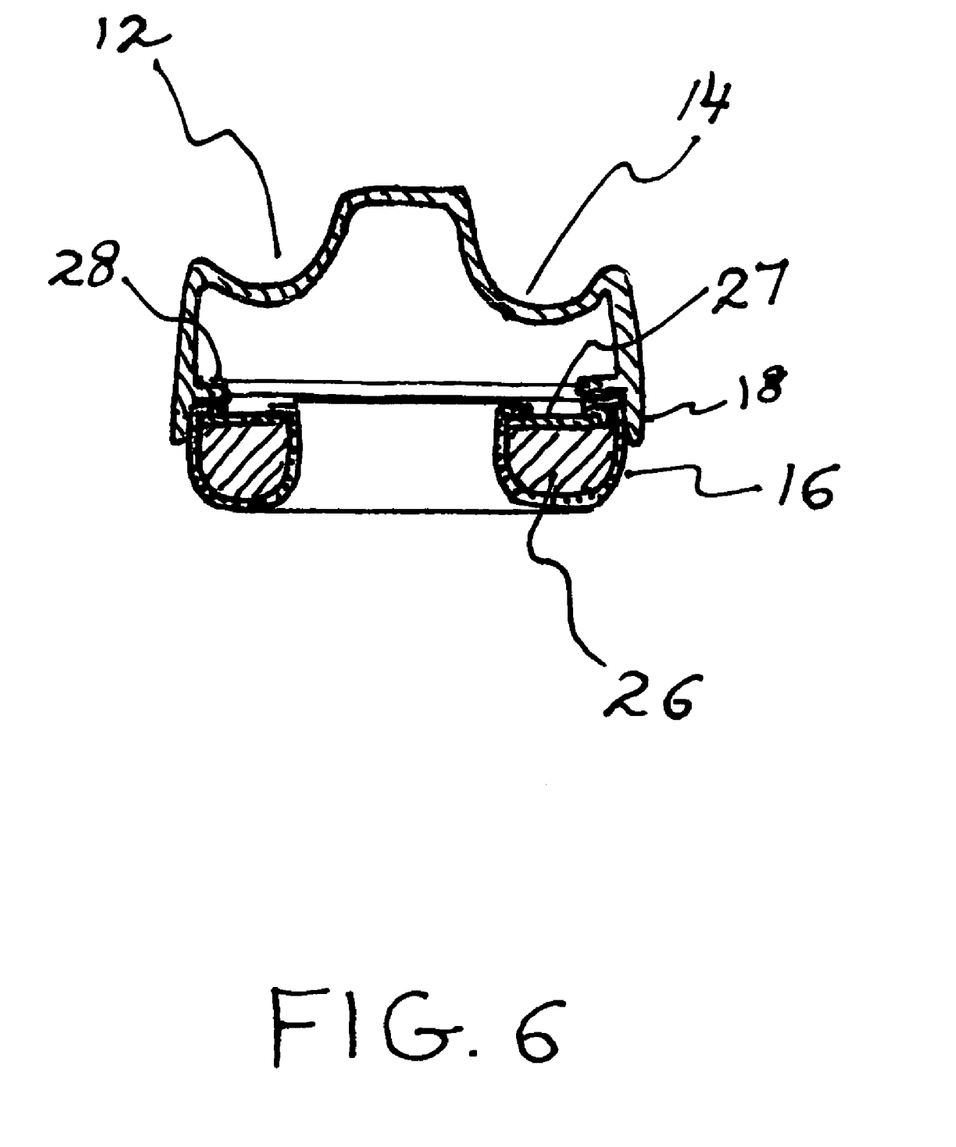
FIG. 6 is a section view of the invention.

FIG. 5 is a top view of the invention 100. Horizontal concave finger channels 8, 10 and vertical finger channels 12, 14 can be clearly seen. Section line 20 is described in FIG. 6. In this view the vertical concave finger channels 12, 14 can be clearly seen. Also resilient panel 16 is shown to be comprised of an internal resilient materiel 26 such as electrometric foam or gel, and an an outer covering of water resistant materiel such as electrometric vinyl 16. The vinyl covering 27 wraps around a support plate 27. The support plate is fixedly mounted to internal flange 28 so that the panel 16 rests securely within the funnel perimeter edge 18.

Figure 7:
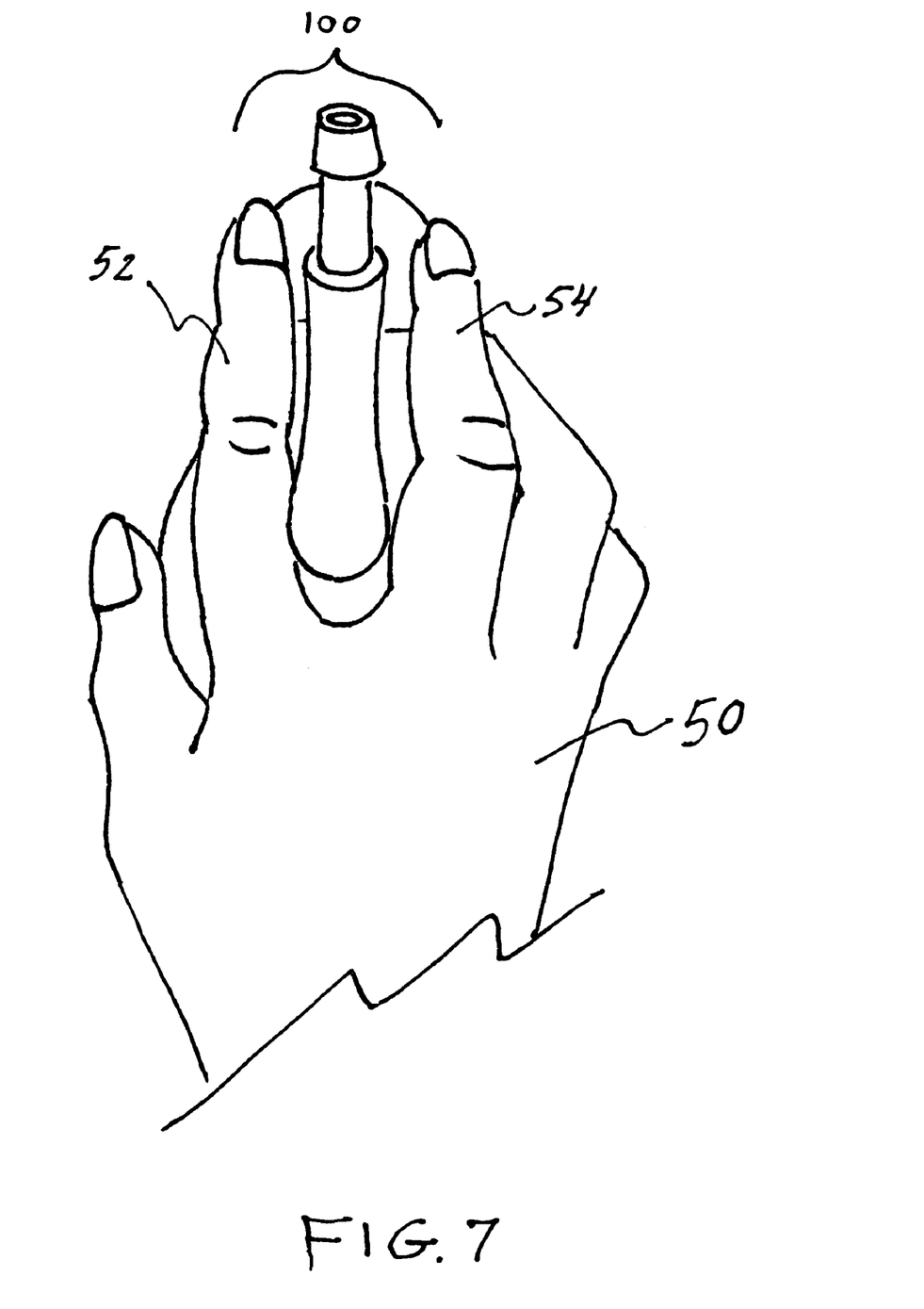
FIG. 7 is a perspective view of the invention being used in the vertical holding position.

FIG. 7 shows a user positioning her hand 50 for use in the vertical finger position where fingers 52, 54 rest in finger channels 12, 14.

Figure 8:
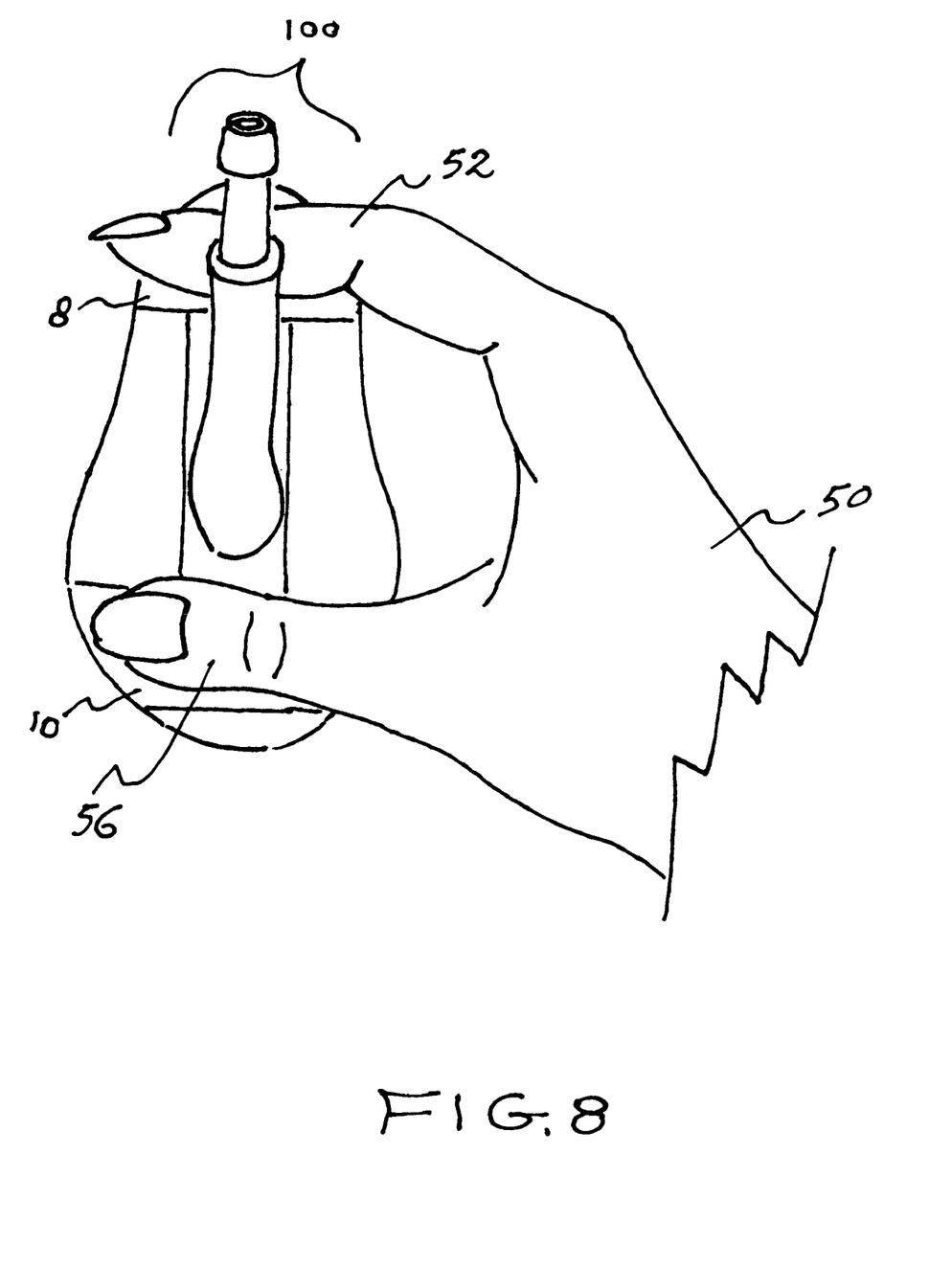
FIG. 8 is a perspective view of the invention being used in the horizontal holding position.

FIG. 8 shows a user positioning her hand 50 for use in the horizontal finger position where fingers 52, 56 in finger channels 8, 10.

The channels 8, 10, 12, 14 are a unique and improved way to securely hold and press the funnel shape 100 of the invention onto the vaginal area of a woman so that the chances of leakage of urine during use are significantly reduced.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A female urinal funnel comprising:
a rigid, essentially ovoid funnel shape having an upper surface with an opening and an opposite lower bottom, said opening forming a perimeter entrance lip having a narrower diameter at its lower portion and a wider diameter at its upper portion; said funnel shape having side walls that extend vertically down from said entrance lip and then curve inwardly at approximately a ninety degrees angle forming said bottom that terminates at an exit orifice located approximately at a middle of said bottom of the funnel, wherein said exit orifice includes a barbed cylindrical tube shape that frictionally accepts a standard half inch flexible tube and wherein said barbed cylindrical tube is extended downwardly from the middle of said funnel and with respect to the plane of said entrance lip at an angle of approximately sixty degrees; said bottom including a pair of concave finger retaining channels located horizontally at the bottom upper and lower portions, and said bottom further including a pair of concave finger retaining channels located vertically at the bottom left and right portions, wherein the channels provide an improved way to securely hold and press the funnel onto the vaginal area of a female so that the chances of leakage of urine during use are significantly reduced.

2. The female urinal funnel as claimed in claim 1 further comprising:
a resilient water resistant panel shaped to fit snuggly over the labia majora of the female; said panel conforming to the plane of the inside perimeter of the entrance lip of said funnel and extending outward beyond the said entrance lip approximately one half of one inch and having a centrally located ovoid aperture at the center of said panel to allow for urine to exit from the female and into said funnel; said panel being constructed of a resilient material including electrometric foam or gel and covered with a smooth, water resistant and flexible covering including electrometric vinyl.

* * * * *